(12) United States Patent
Saiz

(10) Patent No.: US 9,662,193 B1
(45) Date of Patent: May 30, 2017

(54) GAUGE SYSTEM FOR MEASURING UNDERBITE AND OVERBITE IN RUMINANTS

(71) Applicant: Juan Fernando Saiz, Sugar Land, TX (US)

(72) Inventor: Juan Fernando Saiz, Sugar Land, TX (US)

( * ) Notice: Subject to any disclaimer, the term of this patent is extended or adjusted under 35 U.S.C. 154(b) by 0 days.

(21) Appl. No.: 15/144,815

(22) Filed: May 3, 2016

Related U.S. Application Data

(60) Provisional application No. 62/155,452, filed on Apr. 30, 2015.

(51) Int. Cl.
| | |
|---|---|
| *A61C 3/00* | (2006.01) |
| *A61C 19/05* | (2006.01) |
| *A61D 5/00* | (2006.01) |

(52) U.S. Cl.
CPC .............. *A61C 19/05* (2013.01); *A61D 5/00* (2013.01)

(58) Field of Classification Search
CPC .......... A61C 19/04; A61C 19/05; A61D 5/00; A61B 5/1072
USPC ........... 433/1, 141, 147; 33/511–514, 501.11
See application file for complete search history.

(56) References Cited

U.S. PATENT DOCUMENTS

| | | | | |
|---|---|---|---|---|
| 6,430,830 | B1 * | 8/2002 | Segal ..................... | A61C 19/04 33/513 |
| 8,444,415 | B2 * | 5/2013 | Thornton ............... | A61C 19/04 433/215 |

* cited by examiner

*Primary Examiner* — Cris L Rodriguez
*Assistant Examiner* — Matthew Saunders
(74) *Attorney, Agent, or Firm* — Kenneth A. Roddy

(57) ABSTRACT

A gauge system for measuring underbite and overbite in ruminants includes a handle having a spring biased retainer pivotally mounted thereon and a head portion at a front end having a tip receiving aperture, a set of interchangeable underbite measuring tips for use with cattle, a set of interchangeable underbite measuring tips for use with sheep, and a overbite measuring tip. The rear portion of the tip retainer is depressed by a user's thumb to pivot the front portion of the tip retainer upwardly to an open position and expose the tip receiving aperture for insertion or removal of a selected underbite measuring tip, or the overbite measuring tip, and thereafter removing the thumb allows the front portion of the tip retainer member to be lowered under spring pressure to the closed position and retain the selected underbite measuring tip, or the overbite tip in the aperture.

1 Claim, 8 Drawing Sheets

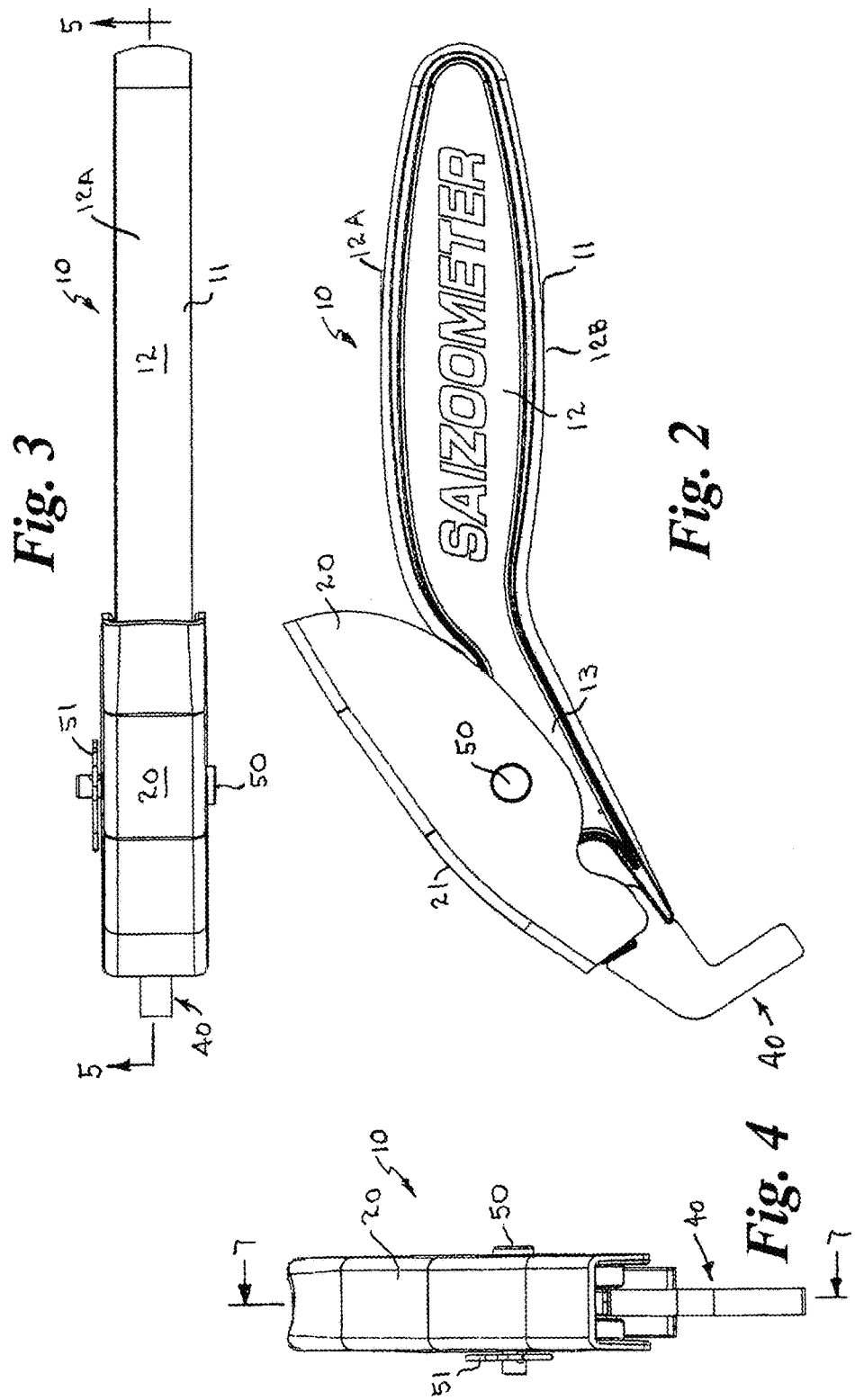

GAUGE SYSTEM FOR MEASURING UNDERBITE AND OVERBITE IN RUMINANTS

CROSS REFERENCE TO RELATED APPLICATION

This application claims priority of U.S. Provisional Application Ser. No. 62/155,452, filed Apr. 30, 2015, the pendency of which is extended until May 2, 2016 under 35 U.S.C. 119(e)(3).

BACKGROUND OF THE INVENTION

1. Field of the Invention

This invention relates generally to instruments for determining jaw defects in animals, and more particularly to a gauge system for measuring underbite (brachygnathia superior) and overbite (brachygnatia inferior) in ruminants.

2. Background Art

All species of ruminants lack top incisors. All these animals have a tough dental pad below their top lip, sometimes referred to as the maxillary pad, instead of front teeth, and a huge gap between the dental pad (maxillary pad) and the back teeth Underbite (brachygnathia superior) and overbite (brachygnatia inferior) in ruminants are well know genetic jaw defects that develop as a result of several factors, including osteogenetic disorder, mechanical factors and heredity, and is characterized by failure of the premaxillary bone to grow to normal length and width.

A normal bite is known as the condition, when the mouth is closed in a bite position and the upper and lower jaw are perfectly aligned, the upper edge of the teeth crown (the part of a tooth external to the gum) is touching the front edge of the dental pad (maxillary pad) of the upper jaw.

Underbite (brachygnathia superior), also known as mandibular prognathism, although the first term is considered most correct, is a condition caused by failure of the premaxillary bone to grow to normal length and width. Prognathism refers to a protruding jaw. It is also called an extended chin. In this condition, when the mouth is closed in a bite position, the upper edge of the teeth crown is disposed forward of the front edge of the dental pad (maxillary pad) of the upper jaw.

Overbite (brachygnathia inferior), also known as mandibular brachygnathia, and commonly called parrot mouth prognathism, is a condition caused by failure of the anterior of the lower jaw forward of the premolars to grow to normal length, causing an abnormal shortness of the lower jaw. In this condition, when the mouth is closed in a bite position, the upper edge of the teeth crown is disposed rearward of the front edge, or anterior angle, of the dental pad (maxillary pad) of the upper jaw.

These jaw defects can lead to serious economic loses in bovine and sheep production systems, because it can seriously affect the grazing animal's ability to bite off foliage and have adequate nutrition.

Therefore it is important to be able identify and quantitatively measure these specific jaw defects in animals in order to select and eliminate those that have this problem, and also to have the ability to quantify the prevalence of underbite (brachygnathia superior) and overbite (brachygnatia inferior) in the animal population.

There are several patents directed toward gauge instruments for measuring various dental conditions. The following are several examples.

Rhein, U.S. Pat. No. 1,327,114, discloses an attachable or permanent depth gauge which is used with dental and medical instruments to for example, measure the length of a root canal. The gauge disclosed has two members, the first member being affixed or attached to the handle of the instrument and the second member being movable with respect to the first. Depth is measured by viewing an indicator which reflects the distance between the second member and the extremity of the instrument. The sliding gauge must be positioned to the zero point before the measurement is taken and the instrument must be removed from the patient's mouth in order to read the scale. Mayer et al. U.S. Pat. No. 4,997,368, discloses an oral measuring insert device having biased top and bottom surfaces which can be directed into the mouth between the frontal upper and lower teeth to measure the opening of the mouth. The device is formed from a lightweight, disposable plastic having arcuate grooves positioned within the upper and lower surfaces providing detents for the teeth. Numerical indicia is disposed along the side of the insert to allow the examiner to quickly determine the degree of movement the mandible has undergone at maximum insertion. Various sizes of the insert may be manufactured and made available for different mouth sizes such as for example with young children, older children or adults.

Sheridan, U.S. Pat. No. 5,044,951, discloses a dental space and periodontal cavity measuring instrument for insertion in interdental or interproximal spaces between teeth and in periodontal cavities in both the upper and lower dental arches to determine the width of such spaces and the depth of the cavities, respectively, for appropriate treatment. The dental space and periodontal cavity measuring instrument has a centrally located handle provided with a pair of oppositely-extending single tips or multiple, elongated, graduated cylinders which terminate in graduated ends, for insertion in the interdental spaces and periodontal cavities. The calibrated cylinders and graduated ends may be extended in a straight line from the handle, or one or more cylinders in one or both of the calibrated and graduated tips may be angulated and the diameter of each cylinder may be indicated on the handle for size-identification purposes. The ends of the cylinder or stem tips may also be "waffled" with striations for ligature tucking purposes.

Urban, U.S. Pat. No. 5,676,544, discloses an instrument for subgingival scaling, root planing and maintenance of periodontal health. The instrument has an elongated body with a handle portion, a terminal shank portion, a working end, and a gauge. The terminal shank portion includes a base having a first portion, which is coaxial with the handle portion, and a second portion, which is angled from the first portion. The working end has a rear heel portion adjacent to the second portion and a front toe portion. Between the heel and toe there is a blade edge extending lengthwise. The gauge is arranged along the annular surface of the second portion of the terminal shank. In order to measure the periodontal health of the patient on whom the instrument is being used, the instrument is inserted into the periodontal space between the tooth and the gum. The depth of the periodontal space is determined by reading the marking on the gauge which meets the gumline.

SUMMARY OF THE INVENTION

The present invention overcomes the aforementioned problems and is distinguished over the prior art in general, and these patents in particular, by a gauge system for measuring underbite (brachygnathia superior) and overbite (brachygnatia inferior) in ruminants. The gauge system includes a handle member having a retainer member pivotally mounted thereon, a set of interchangeable cow underbite measuring tips for use with cattle, a set of interchangeable sheep underbite measuring tips for use with sheep, and an overbite measuring tip.

The handle member has a handgrip portion to be gripped by a hand of a user and a head portion at a front end having a tip receiving aperture. A spring biased tip retainer member is pivotally mounted on the handle member to be pivoted between a normally closed position and an open position, and has a front portion configured to enclose said tip receiving aperture in the closed position and a rear portion configured to receive the thumb of the user's hand. Each of the underbite measuring tips has a rear portion configured to be removably received in the tip receiving aperture and a front portion having a flat rectangular measuring leg that extends perpendicularly downward from the rear portion. The flat measuring leg of each of the underbite measuring tips has a different thickness of a standard unit of measurement that ranges from 2 mm to 8 mm, respectively. The overbite measuring tip has a rear portion configured to be removably received in the tip receiving aperture and a front portion having a vertical leg portion and a horizontal flat rectangular measuring leg that extends forward and perpendicular thereto and terminates at an outer end. The top surface and lateral sides of the flat rectangular measuring leg has a metric scale divided into millimeters with major markings at 5 mm, 10 mm, 15 mm, and 20 mm beginning at the outer end.

The tip retainer member rear portion is depressed by the user's thumb to pivot the front portion of the tip retainer member upwardly to the open position and expose the tip receiving aperture for insertion or removal of a selected underbite measuring tip, or the overbite measuring tip, and thereafter removing the thumb allows the front portion of the tip retainer member to be lowered under spring pressure to the closed position and retain the selected underbite measuring tip, or the overbite tip in the aperture.

BRIEF DESCRIPTION OF THE DRAWINGS

FIGS. 2, 3, and 4 are a side elevation view, top plan view, and a front end elevation view, respectively, of the gauge apparatus in an assembled condition.

DETAILED DESCRIPTION OF THE INVENTION

Figure 1A:
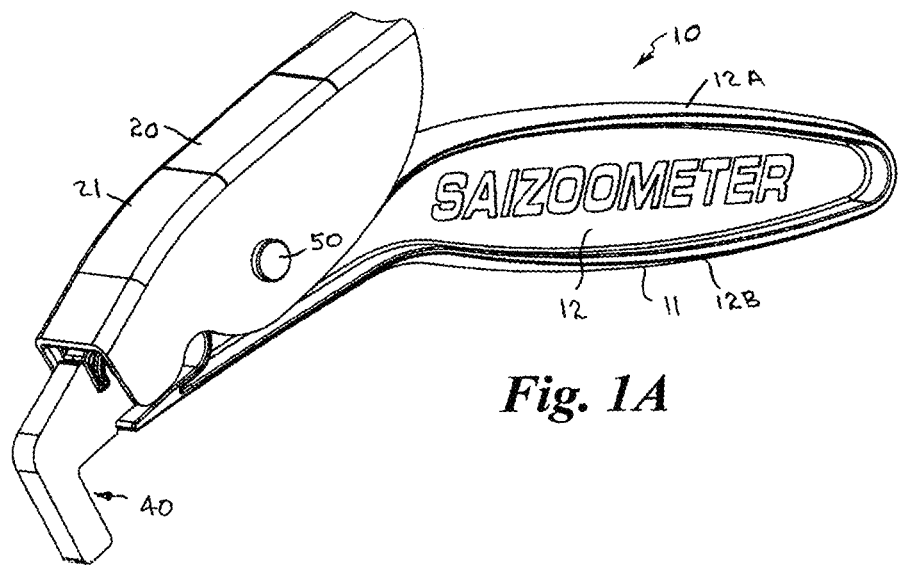
FIGS. 1A and 1B are perspective views of the gauge apparatus in accordance with the present invention with an interchangeable underbite measuring tip installed in the handle member and retained by the retainer member, shown from the front and rear respectively.
Figure 1B:
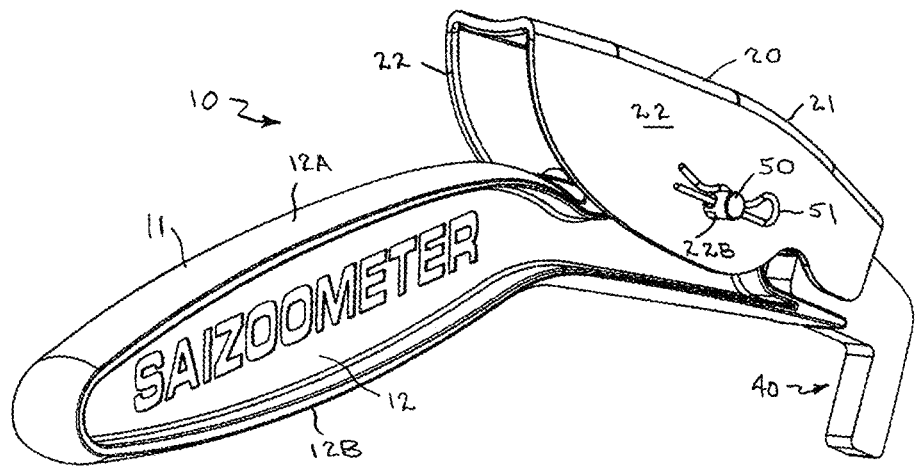

Referring to the drawings by numerals of reference, there is shown in FIGS. 1A, 1B, 2, 3, 4, 5, and 6, an embodiment of a gauge system for measuring underbite (brachygnathia superior) and overbite (brachygnatia inferior) in ruminants.

Figure 7:
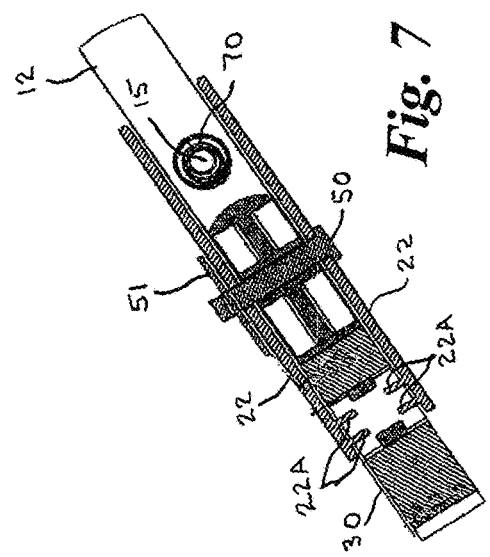
FIG. 7 is a longitudinal cross sectional view taken through the pivot point along line 7-7 of FIG. 4 showing a cow underbite measuring tip retained in the handle member.

The major components of the gauge system include a handle assembly 10, which includes a generally rectangular handle member 11 having a retainer member 20 pivotally mounted on the handle member, a set of seven interchangeable underbite measuring tips 30 for use with cattle (hereinafter referred to as "cow tips 30", and a set of seven interchangeable underbite measuring tips 40 for use with sheep (hereinafter referred to as "sheep tips 40", and a one overbite measuring tip 50. FIGS. 1A, 1B, 2, 3, 4, and 5, show a selected sheep tip 40 retained on the handle member 11 by the retainer member 20, and FIGS. 6 and 7 show a selected cow tip 30 retained on the handle member.

Figure 8:
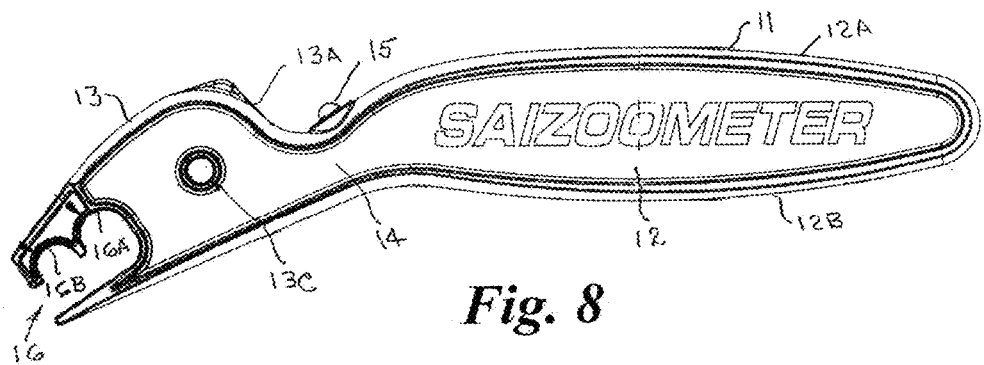
FIG. 8 is a side elevation view of the handle member.
Figure 8A:
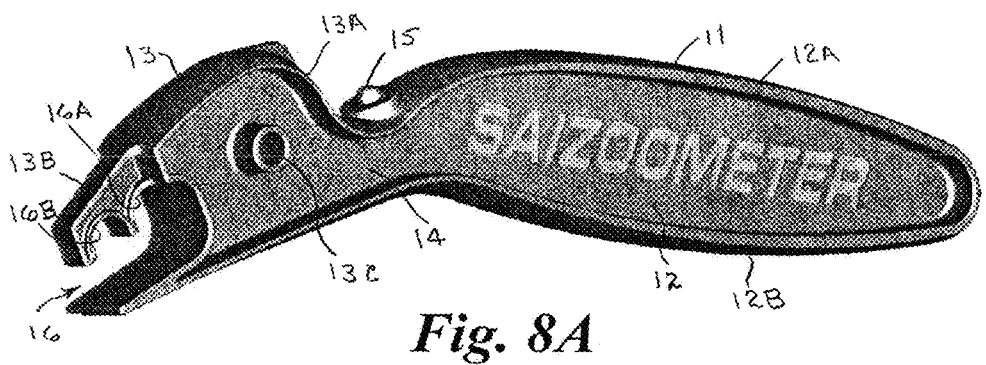
FIGS. 8A and 8B are perspective views of the handle member shown from the front and rear, respectively.
Figure 8B:
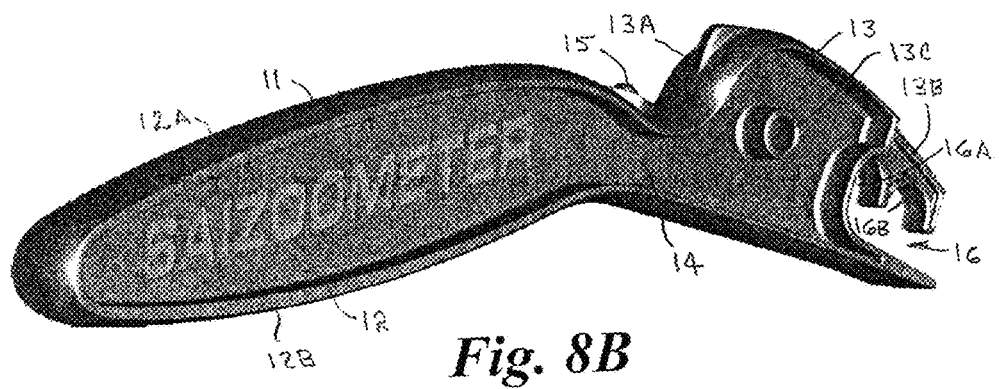
Figure 9A:
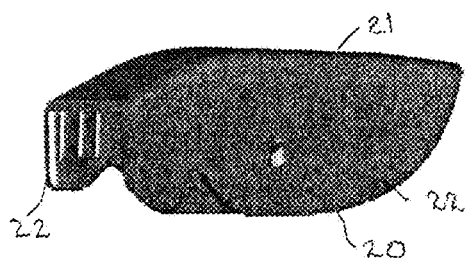
FIGS. 9A and 9B are perspective views of the retainer member shown from the front and rear, respectively.
Figure 9B:
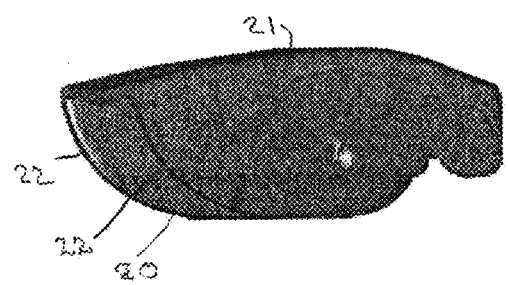
Figure 11:
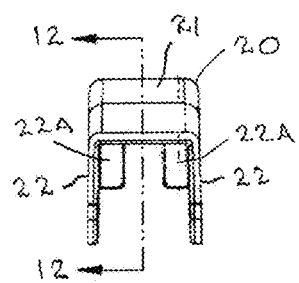
FIGS. 10 and 11 are a side elevation view and a front end view of the retainer member, respectively.
Figure 10:
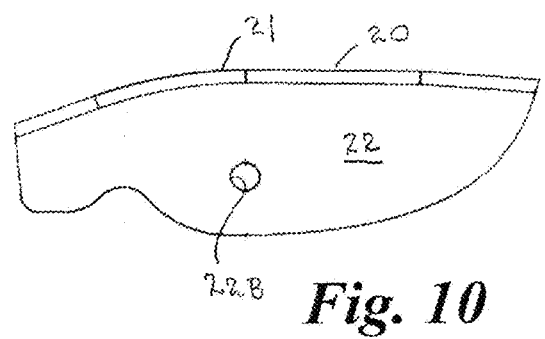
Figure 12:
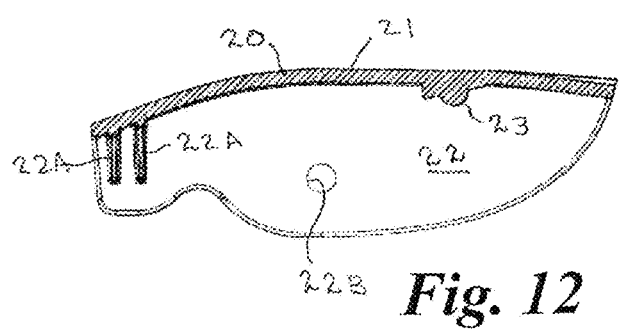
FIG. 12 is a cross sectional view of the retainer member, taken along line 12-12 of FIG. 11.
Figure 13A:
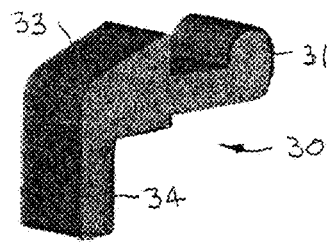
FIGS. 13A and 13B are perspective views of a sheep underbite measuring tip shown from the front and rear, respectively.
Figure 13B:
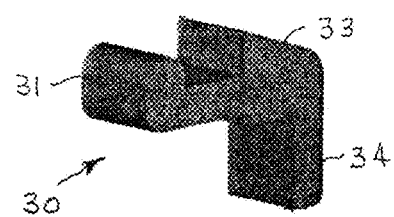
Figure 15:
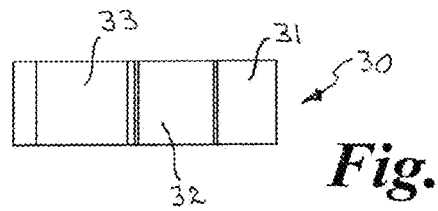
FIGS. 14, 15, and 16 are a side elevation view, a top end view, and a rear end view of the sheep underbite measuring tip, respectively.

Referring additionally to FIGS. 8, 8A, and 8B, the handle member 11 has a rear hand grip portion 12 which can be gripped with the right or left hand of a user with opposed arcuate curved top and bottom surfaces 12A and 12B for receiving the hand and fingers of the user, and a head portion 13 at the front end of the handle member adjoined thereto by an intermediate portion 14 of reduced height. The head portion 13 and the intermediate portion 14 extend angularly downward and forward from the hand grip portion at a slight angle relative to a horizontal axis.

The top end of the head portion 13 has an outwardly and downwardly curved rear portion 13A that adjoins the top of the intermediate portion 14 and has a front end portion 13B of narrower width. A raised rounded boss 15 is formed on the top surface of the intermediate portion 14 adjacent to its juncture with the hand grip portion 12. A hole 13C extends transversely through the head portion 13, and a slot 16 extends transversely through the head portion 12 disposed forward of the hole 13A which is configured to slidably receive a selected cow tip 30 or sheep tip 40 from either side of the slot. The slot 16 has an open front end, a flat bottom surface, a semicircular rear end, and a top surface that has a first upwardly curved larger radius rear cavity 16A adjoining the semicircular rear end, and an adjacent second upwardly curved smaller radius front cavity 16B spaced a short forwardly therefrom.

Referring additionally to FIGS. 9A, 9B, 10, 11, and 12, the retainer member 20 has a generally inverted U-shaped configuration with an arcuate slightly curved top wall 21 and a pair of laterally opposed side walls 22 that are slidably received on, and straddle, the head portion 13 of the handle member 11. A rounded boss 23 is formed on the underside of the top wall 21 near its rearward end, and a pair of parallel closely spaced tabs 22A are formed on the interior surface of each side wall 22, respectively, near their front ends and extend a short distance inwardly from the side walls in opposed relation and terminate a distance from the side walls to define an interior space therebetween. When the retainer member 20 is mounted on the handle member 11, the tabs 22A are slidably disposed on opposed outer sides of the narrower width portion 13B at the top end of the head portion 13 of the handle member and straddle the laterally opposed open ends of the second upwardly curved smaller radius front cavity 16B. A hole 22B is formed in each of the laterally opposed side walls 22 in axial alignment.

The retainer member 20 is pivotally mounted on the handle member 11 by passing the shank of a clevis pin 50 through the axially aligned holes 13A and 22B in the handle member and the sidewalls 22 of the retainer member 20, and installing a cotter pin 51 through a hole in the outer end of the clevis pin shank.

Figure 5:
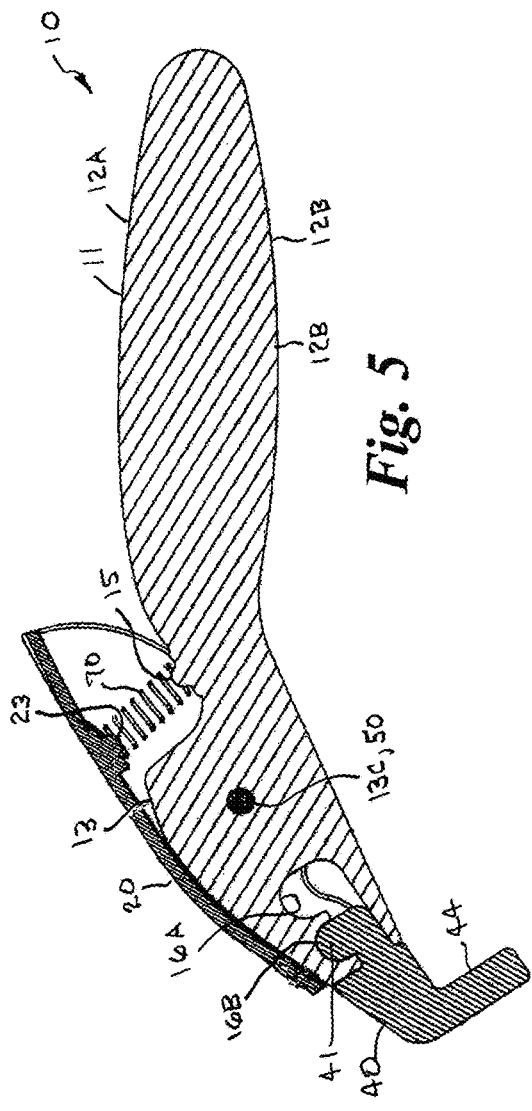
FIG. 5 is a longitudinal cross sectional view of the gauge apparatus taken along line 5-5 of FIG. 3 with a sheep underbite measuring tip retained in the handle member.
Figure 6:
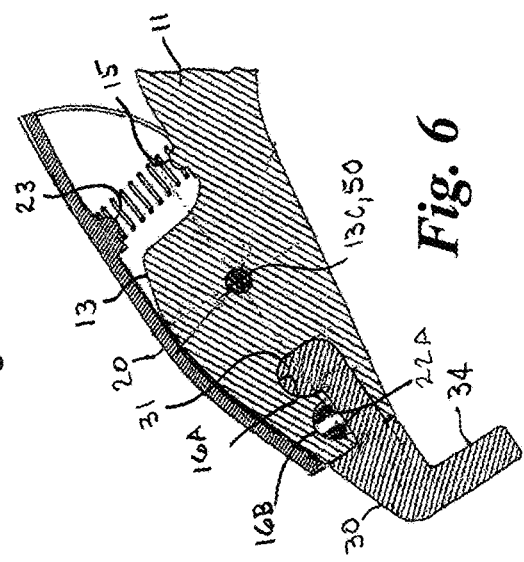
FIG. 6 is a partial longitudinal cross sectional view of the gauge apparatus, similar to FIG. 5, showing a cow underbite measuring tip retained in the handle member.

As best seen in FIGS. 5 and 6, a compression spring 70 is mounted between the handle member 11 and the retainer member 20 by engaging one end of the spring on the rounded boss 15 on the top surface of the intermediate portion 14 of the handle and its opposed end on the rounded boss 23 on the underside of the top wall 21 of the retainer member 20. The compression spring 70 urges the retainer member to a normally closed or retaining position wherein the rear portion of the retainer member is pivoted to a raised position and the lower front portion of its lateral sidewalls 22 straddle and enclose the lateral sides of the head portion 13 of the handle member 11 and the slot 16 and its larger radius rear cavity 16A and smaller radius front cavity 16B.

The retainer member 20 is moved to an open position by a user gripping the hand grip portion 12 of the handle 11 in their hand, placing their thumb on the top surface at the rear of the retainer member, and pressing downward until the bottom surface of the front portion of the retainer member is raised to expose the lateral sides of the head portion 13 of the handle member and the slot 16 with its larger radius rear cavity 16A and smaller radius front cavity 16B.

As mentioned briefly above, the gauge system includes a set of seven interchangeable underbite measuring tips 30 for use with cattle (hereinafter referred to as "cow tips 30", and a set of seven interchangeable underbite measuring tips 40 for use with sheep (hereinafter referred to as "sheep tips 40", and a one overbite measuring tip 60. FIGS. A, 1B, 2, 3, 4, and 5, show a selected sheep tip 40 retained on the handle member 11 by the retainer member 20, and FIGS. 6 and 7 show a selected cow tip 30 retained on the handle member.

Figure 14:
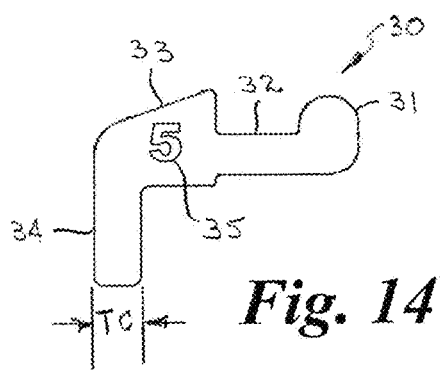
Figure 16:
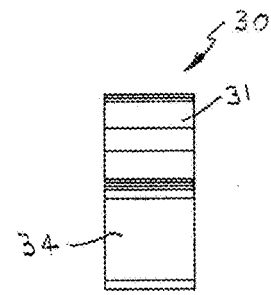
Figure 17A:
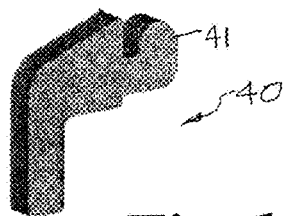
FIGS. 17A and 17B are perspective views of a cow underbite measuring tip shown from the front and rear, respectively.
Figure 17B:
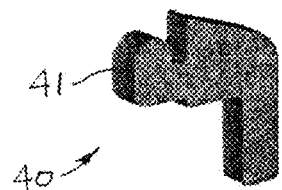
Figure 19:
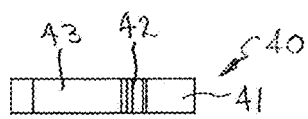
FIGS. 18, 19, and 20 are a side elevation view, a top end view, and a rear end view of the cow underbite measuring tip, respectively.

Referring additionally to FIGS. 13A, 13B, 14, and 15, each of the underbite measuring cow tips 30 is a generally inverted L-shaped configuration having a semi-circular rear portion 31 sized and shaped to be slidably received in the larger radius rear cavity 16A of the slot of the head portion 13, and an adjoined smaller rectangular intermediate portion 32 that is sized and shaped to be slidably received in the slot 16 of the handle member 11 from either lateral side of the handle member. The smaller rectangular portion 32 of each underbite measuring cow tip 30 adjoins a larger rectangular portion 33 which is sized and shaped to engage the flat front end of the head portion 13 of the handle member when the interchangeable tip is installed the slot. A flat rectangular measuring leg 34 extends perpendicularly downward from the front end of the larger rectangular portion. The thickness TC of the flat rectangular measuring leg 34 is different for each one of the seven underbite measuring cow tips 30. More particularly, the thickness TC of each of the underbite measuring cow tips 30 is of a standard unit of measurement that ranges from 2 mm to 8 mm, respectively. As seen in FIG. 14, each of the underbite measuring cow tips 30 may be provided with a numeral 35 on each side of the larger rectangular portion that corresponds to the respective unit of measurement.

Table 1 below illustrates an example of a numbering system that may be utilized for easily and quickly identifying the respective underbite measuring cow tips 30.

TABLE 1

| COW TIP NUMERAL | THICKNESS "TC" | |
|---|---|---|
| | MM | INCH |
| 2 | 2 | .079 |
| 3 | 3 | .118 |
| 4 | 4 | .157 |
| 5 | 5 | .197 |
| 6 | 6 | .236 |
| 7 | 7 | .275 |
| 8 | 8 | .315 |

Figure 18:
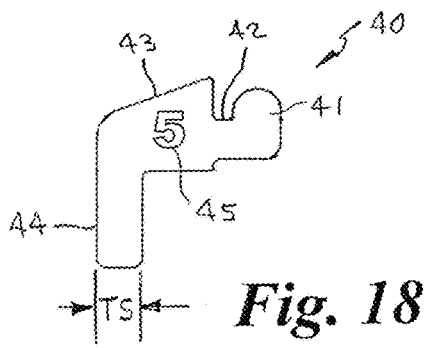
Figure 20:
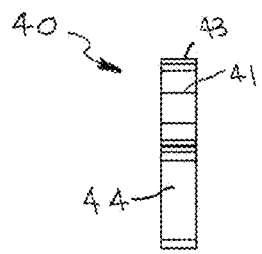
Figure 21A:
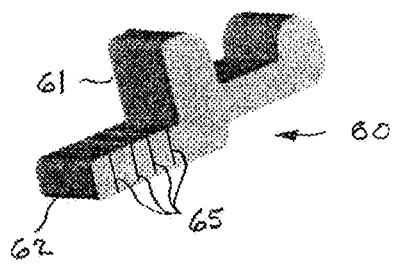
FIGS. 21A and 21B are perspective views of an overbite measuring tip shown from the front and rear, respectively.
Figure 21B:
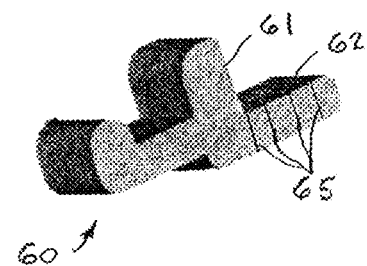
Figure 21D:
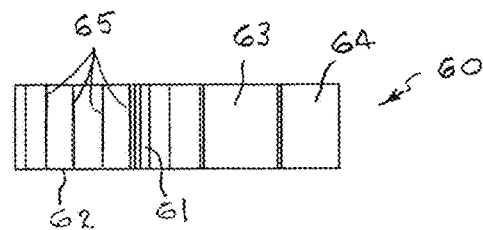
FIGS. 21C and 21D are a side elevation view and a top end view of the overbite measuring tip, respectively.
Figure 21C:
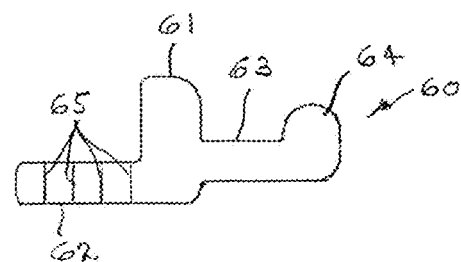

Referring additionally to FIGS. 17A, 17B, 18, 19, and 20, each of the underbite measuring sheep tips 40 is also a generally inverted L-shaped configuration similar to the cow tips, but narrower in width. Each of the underbite measuring sheep tips 40 has a semi-circular rear portion 41 sized and shaped to be slidably received in the smaller radius front cavity 16A of the slot of the head portion 13, and an adjoined smaller rectangular intermediate portion 42 that is sized and shaped to be slidably received in the slot 16 of the handle member 11 from either lateral side of the handle member. The smaller rectangular portion 42 of each underbite measuring sheep tip 40 adjoins a larger rectangular portion 43 which is sized and shaped to engage the flat front end of the head portion 13 of the handle member when the interchangeable tip is installed the slot. A flat rectangular measuring leg 44 extends perpendicularly downward outward from the front end of the larger rectangular portion. The thickness TS of the flat rectangular measuring leg 44 is different for each one of the seven underbite measuring sheep tips 40. More particularly, the thickness TS of each of the underbite measuring sheep tips 40 is of a standard unit of measurement that ranges from 2 mm to 8 mm, respectively. As seen in FIG. 18, each of the underbite measuring sheep tips 40 may be provided with a numeral 45 on each side of the larger rectangular portion that corresponds to the respective unit of measurement.

Table 2 below illustrates an example of a numbering system that may be utilized for easily and quickly identifying the respective underbite measuring sheep tips 40.

TABLE 2

| SHEEP TIP NUMERAL | THICKNESS "TC" | |
|---|---|---|
| | MM | INCH |
| 2 | 2 | .079 |
| 3 | 3 | .118 |
| 4 | 4 | .157 |
| 5 | 5 | .197 |
| 6 | 6 | .236 |

TABLE 2-continued

| SHEEP TIP | THICKNESS "TC" | |
| --- | --- | --- |
| NUMERAL | MM | INCH |
| 7 | 7 | .275 |
| 8 | 8 | .315 |

Because the underbite measuring sheep tips 40 are narrower than the cow tips 30, they are retained in the smaller radius front cavity 16A of the slot of the head portion 13 of the handle member by the inwardly facing closely spaced tabs 22A on the interior surface of each side wall 22 of the retainer member 20 which straddle the lateral sides of the smaller radius front cavity when the retainer is in the spring biased closed position.

Referring now to FIGS. 21A, 21B, 21C, and 21D, the overbite measuring tip 60 is a generally L-shaped configuration having a vertical rectangular leg portion 61 and a horizontal flat rectangular measuring leg portion 62 extending forward and perpendicular thereto. The back side of the vertical leg portion 61 has a horizontal rectangular portion extending a short distance rearwardly therefrom terminating in a semi-circular rear end portion which are sized and shaped to be slidably received in the larger radius rear cavity 16A of the slot 16 of the head portion 13 of the handle member 11 from either lateral side of the handle member, respectively. When the overbite measuring tip 50 is received in the slot of the handle member, the back side of the vertical rectangular leg portion 61 is disposed against the front end of the head portion 13 of the handle member and the flat rectangular measuring leg portion 62 extends outwardly a distance beyond the front end of the handle member 11. The top surface and lateral sides of the flat rectangular measuring leg 62 are provided with a metric scale divided into millimeters with major divisional lines 65 at 5 mm, 10 mm, 15 mm, and 20 mm beginning at the outer end of the measuring leg.

Tool Assembly

To install a selected underbite measuring tip 30, 40, or the overbite measuring tip 50 into the handle member member 11, the handle is held gripped by one hand (right or left hand) of the user, and the retainer member 20 is pivoted to the opened position by the user's thumb to expose the slot 16 and its larger radius rear cavity 16A and smaller radius front cavity 16B of the head portion 13. The selected underbite measuring tip or overbite measuring tip is aligned with the slot 16 and cavity 16A or 16B and pressed into the slot and cavity from either lateral side of the handle with the user's other hand. The retainer member is closed by relieving the downward pressure exerted by the user's thumb such that the front portion of the retainer member covers the slot and rear portion of the underbite or overbite measuring tip installed therein, to releasably secure the selected measuring tip to the handle.

When an underbite measuring tip is secured in the handle member, the flat rectangular measuring leg extends downwardly a distance beyond the front end of the handle member. When the overbite measuring tip is secured in the handle member, the flat rectangular measuring leg portion bearing the scale extends forwardly a distance beyond the flat front end of the handle member.

These steps are reversed to remove the selected underbite measuring tip or overbite measuring tip from the handle member.

Operation

After the selected underbite measuring tip or the overbite measuring tip has been secured to the handle, the tool is ready to be used to accurately measure the underbite or overbite condition of the animal depending upon the tip that was installed.

It is recommended that at least two people be present in order to make a proper measurement of the animal's bite; one person that holds and opens the animal's mouth, and another person that places the tool in the animal's mouth and measures the bite.

The animal is placed in a location where its head can be safely held still in a secure manner, not only for the animal, but also for the safety of the person holding the animal for the person that is using the measuring tool.

A muzzle is placed on the animal's head to immobilize and prevent the animal from moving its head.

After the animal's head is immobilized and with its mouth in a closed biting position, one person places both hands with the fingers facing up and the palm in front of the animal's lips, then, using their fingers to open the lips, to make sure the animal stays in a biting position with the mouth closed.

Normal Bite Condition

With the animal's lips open and its mouth closed in the bite position, if it is seen that the upper and lower jaw are perfectly aligned, the edge of the teeth or crown should be touching the front edge of the dental pad (maxillary pad) in the upper jaw of the animal, this is considered to be a normal bite condition.

Underbite Condition

If the crown of the lower teeth is not touching the dental pad (maxillary pad) in the mouth closed, bite position, it means that the animal has an unusual bite or an underbite, and in which case the underbite measuring tips are is used to measure the distance between the back of the teeth and the gum at the top of the edge of the dental pad (maxillary pad).

This is accomplished, with the animal's mouth closed in the bite position and the lips open, by placing the flat rectangular measuring leg of the underbite measuring tip attached to the handle member in the space between the teeth and the dental pad (maxillary pad). In order to achieve an exact measurement, the thickness of the flat rectangular measuring leg of the underbite measuring tip has to fit perfectly in the space between the back of the teeth and the front edge of the dental pad (maxillary pad). Thus, it may require changing the tips until you find the one having the proper thickness (i.e., from 2 mm to 8 mm) to perfectly fit the space between the back of the teeth and the front edge of the dental pad (maxillary pad). This allows the exact measure according to the thickness (millimeter number) of the tip used.

Overbite Condition

If the crown of the lower teeth touches the dental pad (maxillary pad) behind the anterior angle of the dental pad, it means that the animal has an overbite, and in which case, the overbite measuring tip is used to measure the space between the lower teeth and the anterior angle of the dental pad. This is accomplished, with the animal's mouth closed in the bite position and the lips open, by placing the overbite measuring tip in the front part of the teeth with the rectangular measuring leg portion extending to the anterior angle of the dental pad (maxillary pad), and reading the scale to determine the distance between the teeth and how far they are from the dental the dental pad (maxillary pad).

While the present invention has been disclosed in various preferred forms, the specific embodiments thereof as disclosed and illustrated herein are considered as illustrative only of the principles of the invention and are not to be considered in a limiting sense in interpreting the claims. The claims are intended to include all novel and non-obvious combinations and sub-combinations of the various elements, features, functions, and/or properties disclosed herein. Variations in size, materials, shape, form, function and manner of operation, assembly and use, are deemed readily apparent and obvious to one skilled in the art from this disclosure, and all equivalent relationships to those illustrated in the drawings and described in the specification are intended to be encompassed in the following claims defining the present invention.

The invention claimed is:

1. A gauge system for measuring underbite (brachygnathia superior) and overbite (brachygnatia inferior) in ruminants, comprising:

a handle assembly including a handle member having a handgrip portion to be gripped by a hand of a user and a head portion at a front end having a tip receiving aperture;

a spring biased tip retainer member pivotally mounted on said handle member to be pivoted between a normally closed position and an open position, said retainer having a front portion configured to enclose said tip receiving aperture in said closed position and a rear portion configured to receive the thumb of the user's hand;

a set of interchangeable underbite measuring tips, each having a rear portion configured to be removably received in said tip receiving aperture and a front portion having a flat rectangular measuring leg that extends perpendicularly downward from said rear portion, said flat measuring leg of each of said underbite measuring tips having a different thickness of a standard unit of measurement that ranges from 2 mm to 8 mm, respectively; and an overbite measuring tip having a rear portion configured to be removably received in said tip receiving aperture and a front portion having a vertical leg portion and a horizontal flat rectangular measuring leg that extends forward and perpendicular thereto and terminates at an outer end, a top surface and lateral sides of said flat rectangular measuring leg having a metric scale divided into millimeters with major markings at 5 mm, 10 mm, 15 mm, and 20 mm beginning at said outer end;

said tip retainer member rear portion capable of being depressed by the user's thumb to pivot said front portion of said tip retainer member upwardly to said open position and expose said tip receiving aperture for insertion or removal of a selected said underbite measuring tip, or said overbite measuring tip, and thereafter removing the thumb to allow said front portion of said tip retainer member to be lowered under spring pressure to said closed position and retain said selected underbite measuring tip, or said overbite tip in said tip receiving aperture.

* * * * *